United States Patent [19]

Sommer et al.

[11] Patent Number: 4,763,661
[45] Date of Patent: Aug. 16, 1988

[54] FILTERED ULTRASONIC WAVE METHOD AND APPARATUS FOR DETECTING DISEASED TISSUE

[75] Inventors: F. Graham Sommer, Stanford; Roger A. Stern, Palo Alto, both of Calif.

[73] Assignee: Stanford University, Stanford, Calif.

[21] Appl. No.: 828,954

[22] Filed: Feb. 11, 1986

[51] Int. Cl.⁴ .............................................. A61B 10/00
[52] U.S. Cl. ......................................... 128/660; 73/602
[58] Field of Search ......................... 73/597, 599, 602; 128/660

[56] References Cited

U.S. PATENT DOCUMENTS

| | | | |
|---|---|---|---|
| 4,228,804 | 10/1980 | Holasek et al. | 128/660 |
| 4,414,850 | 11/1983 | Miwa et al. | 128/660 X |
| 4,437,348 | 3/1984 | Sasaki | 73/626 X |
| 4,442,713 | 4/1984 | Wilson et al. | 128/660 X |
| 4,442,715 | 4/1984 | Brisken et al. | 128/660 X |
| 4,446,737 | 5/1984 | Hottier | 73/602 |

OTHER PUBLICATIONS

Sommer, F. G. et al., "UTS Characterization of Abdominal Tissues via Digital Analysis of Backscattered Waveforms", Radiology, V. 141, #3, Dec. 1984.
Ophir, J. et al., "A Narrowband Pulse-Echo Technique for In Vivo UTS Attenuation Estimation", IEEE BME Trans., vol. 32, No. 3, Mar. 1985, pp. 205-211.
Wells, P. N. T., et al., "Quantitative A-Scan Analysis of Normal & Cirrhotic Liver", Proceedings Seminar UTS Tissue Char., NBS Gaithersburg, M.D., May 28-30, 1975, pp. 61-70.
Shawker, T. H. et al., "UTS Tissue Characterization: Fundamental Concepts & Clinical Application", UTS Annual 1985, ed. by Sanders & Hill, Raven Press, N.Y., 1985 pp. 93-128.
Kuc, R., "Clinical Application of an UTS Attenuation Coefficient Estimation Technique for Liver Pathology Characterization", IEEE BME Trans., V 27, #6, 6/1980, pp. 312-318.
Kuc, R. et al., "Estimating the Acoustic Attenuation Coefficient Slope for Liver from Reflected Ultrasound Signals", IEEE Trans. Sonics & UTS, vol. SU-26, No. 5, Sep. 1979, pp. 353-362.
Parker, K. et al., "Measurement of UTS Attenuation within Regions Selected from B-Scan Images", IEEE Trans., vol. BME-30, No. 8, Aug. 1983, pp. 431-437.
Ophir, J. et al., "Attenuation Estimation in Reflection: Progress & Prospects", UTS Imaging No. 6, (1984), pp. 349-395.
Jones, J. E. et al., "Ultrasonic Tissue Characterization: A Review", Acta Electronica, 26, 1-2, 1984, pp. 3-31.

Primary Examiner—Francis J. Jaworski
Attorney, Agent, or Firm—Fleher, Hohbach, Test, Albritton & Herbert

[57] ABSTRACT

Diseased tissue such as cirrhotic liver is differentiated from normal tissue by applying an ultrasound wave to the tissue, receiving backscattered ultrasound waves therefrom and bandpass filtering electrical signals generated from the backscattered wave. Assuming that the ultrasound wave has a spectrum and a center frequency, the bandpass is narrow relative to the spectrum and centered within the bounds of the spectrum of the ultrasound wave. The filtered signal will have an amplitude distribution for diseased tissue which is different from the amplitude distribution of normal tissue.

9 Claims, 3 Drawing Sheets

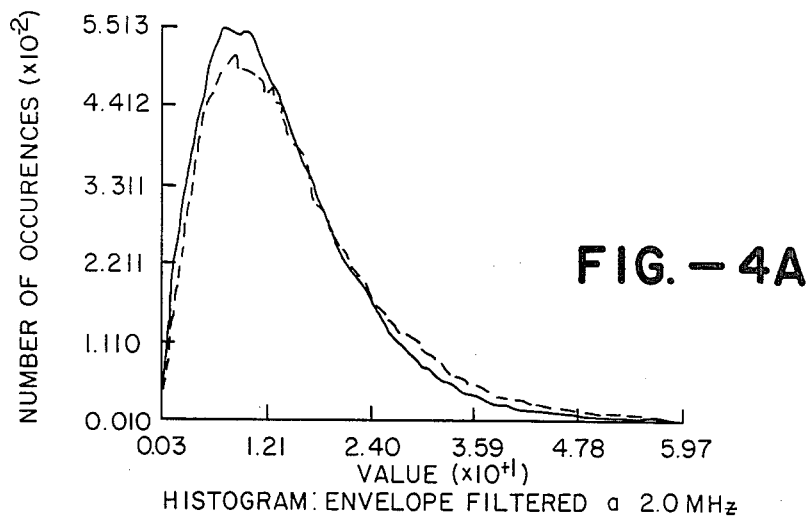
FIG.—4A
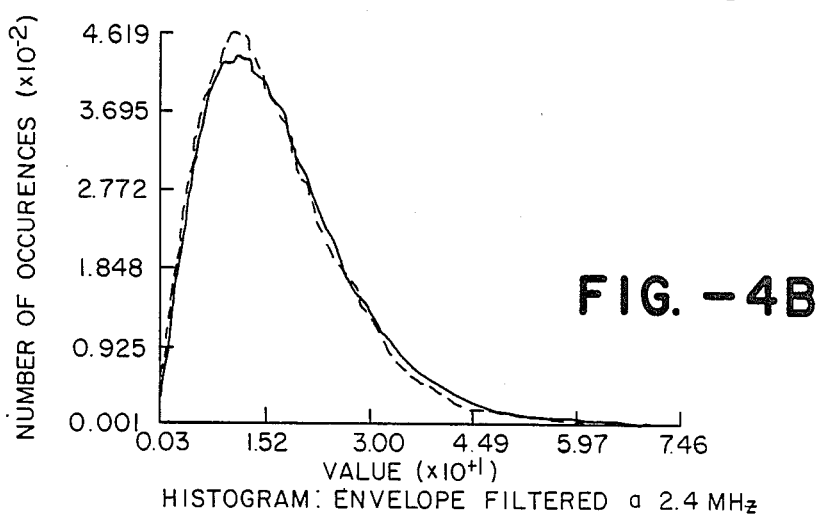
FIG.—4B
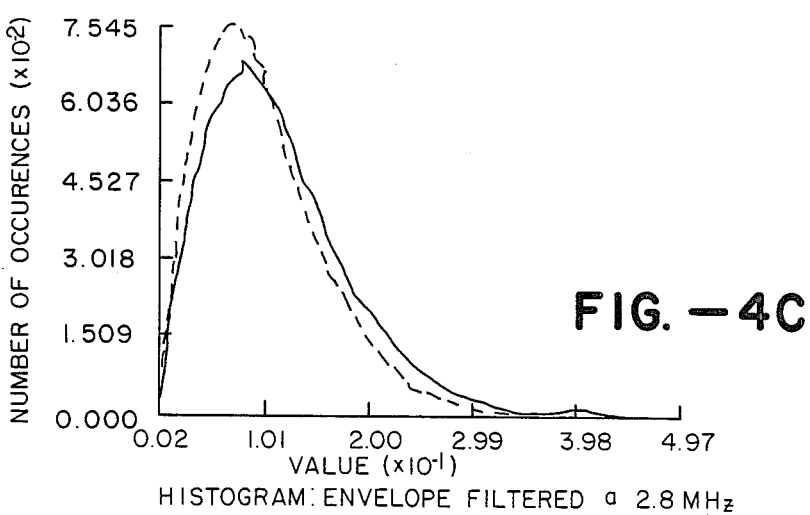
FIG.—4C

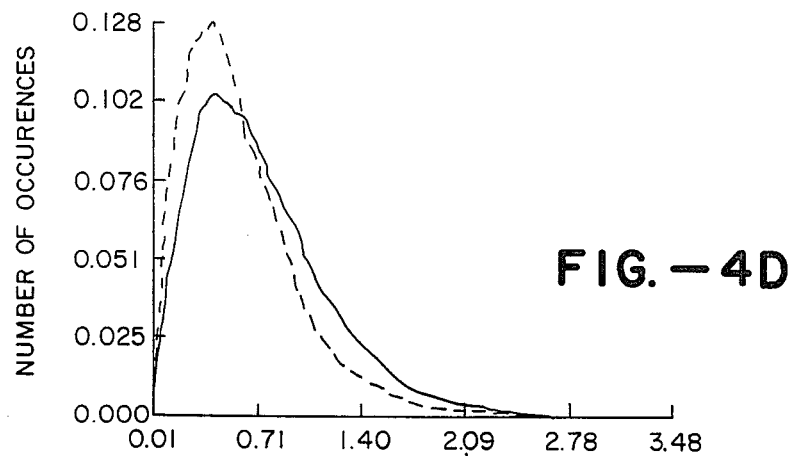
FIG.—4D
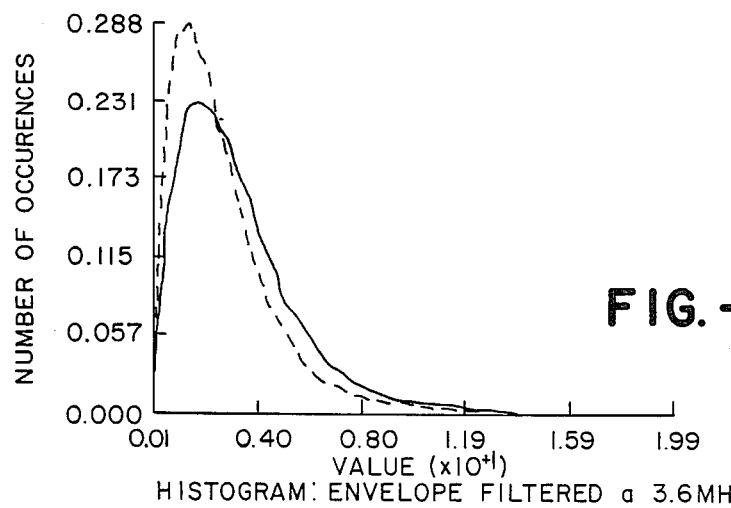
FIG.—4E
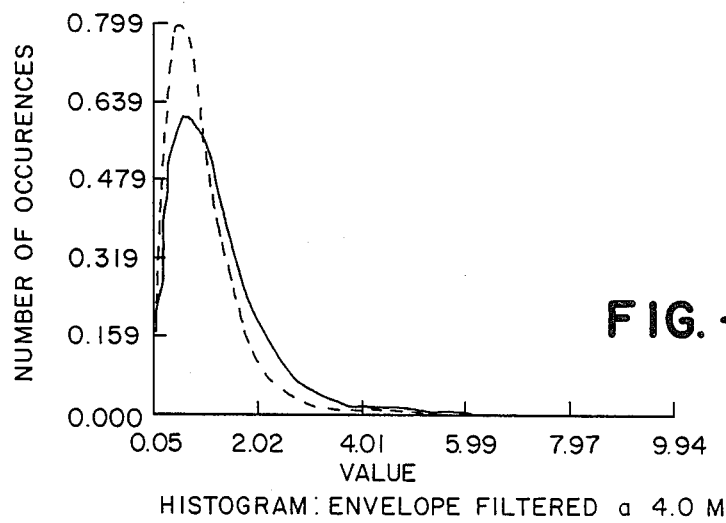
FIG.—4F

FILTERED ULTRASONIC WAVE METHOD AND APPARATUS FOR DETECTING DISEASED TISSUE

The U.S. Government has rights in the disclosed and claimed invention pursuant to NIH/NCI Grant No. CA 37483.

This invention relates generally to ultrasound scanners as used for medical diagnostic purposes, and more particularly the invention relates to the detection of diseased tissue using ultrasound.

Ultrasound scanners are conventionally employed to obtain images of body tissue and organs for medical diagnostic purposes. Briefly, transducers transmit ultrasonic waves (e.g. on the order of several megahertz frequency) into a region under examination, and the transducers generate electrical signals in response to ultrasonic waves backscattered from the region. The magnitude and frequency of the backscattered waves are a function of the composition of the backscattering tissue in organs, and by suitably processing the electrical signals generated by the transducers an image of the examined region can be displayed. The electrical signals generated by the transducers are passed through a variable gain amplifier to compensate for attenuation of the ultrasonic wave in passing through tissue. The time gain function as well as the image or gray scale may be controlled by the system operator.

While different tissues and organs have different ultrasonic backscattering characteristics that allow imaging, heretofore many diseases could not be detected by ultrasound examination. In particular, a normal liver and a cirrhotic liver will generally appear the same in a conventional ultrasound image. However, it has been discovered by the applicants that unfiltered backscattered ultrasound waves that had been recorded in a standardized dynamic range and subsequently filtered with a narrow band filter of center frequency lower than the mean frequency of backscattered ultrasound, both higher mean amplitude and higher amplitude variance were observed for cirrhotic liver compared to normal liver. For higher than mean center frequency narrow band filtration, higher mean amplitudes were observed for normal compared to cirrhotic liver.

In accordance with the invention, diseased tissue having relatively large scatterers compared to normal tissue, such as cirrhotic liver tissue, is distinguished from normal tissue by processing backscattered ultrasonic waves therefrom through use of narrow band filters having center frequencies within the spectrum of backscattered waves. By comparing the filtered signal outputs with filtered signal outputs for normal known tissue, the diseased tissue can be identified.

More particularly, an ultrasound wave is applied to the tissue, the ultrasound wave having a first frequency spectrum and a center frequency. The backscattered ultrasonic waves from the tissue are received by a transducer and electrical signals are generated therefrom. The unfiltered received signals are then selectively amplified to a specific dynamic amplitude range prior to recording and further processing. The amplified electrical signals are then passed through at least one bandpass filter which has a narrow pass band relative to the frequency spectrum of the received ultrasound wave and a center frequency which is contained within the bounds of the received frequency spectrum. The amplitude distributions of the filtered signals are then determined and compared with the amplitude distributions for filtered electrical signals for known normal tissue.

In accordance with another feature of the invention, the diseased tissue can be differentiated from normal tissue in an image by suitably weighting the filtered signal to emphasize the difference in amplitude distributions of the filtered signals from the diseased tissue compared to normal tissue.

The invention and objects and features thereof will be more readily apparent from the following detailed description and appended claims when taken with the drawing, in which:

FIGS. 4A–4F are amplitude histograms of filtered electrical signals based on ultrasound reflections from normal tissue and diseased tissue.

Figure 1:
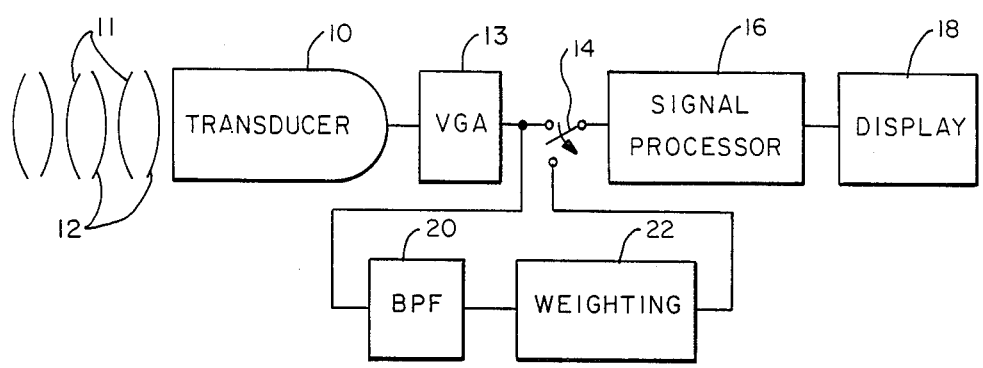
FIG. 1 is a functional block diagram of an ultrasound imaging system including a narrow bandpass filter apparatus in accordance with the present invention.

Referring now to the drawings, FIG. 1 is a functional block diagram of ultrasound imaging apparatus including the present invention. A transducer 10 generates ultrasonic waves 11 which are directed into a volume under examination and receives ultrasound echos 12 from the region undergoing examination. The electrical signals generated by transducer 10 in response to the echoes are applied to a variable gain amplifier 13 which variably amplifies the signals to compensate for attenuation of the waves in passing through tissue. Conventionally, the amplified signals from amplifier 13 are passed through a switch 14 to a signal processor 16. Signal processor 16 generates video control signals with grey scale weighting of the processed signals for controlling a display 18.

In accordance with the invention the amplified signals from amplifier 13 are passed through one or more bandpass filters 20 with the filtered signals suitably weighted at 22 and then applied through switch 14 to the signal processor 16. As will be described further hereinbelow, the bandpass filtered signals when suitably weighted can be used to project an image of normal and diseased tissue.

Figure 2:
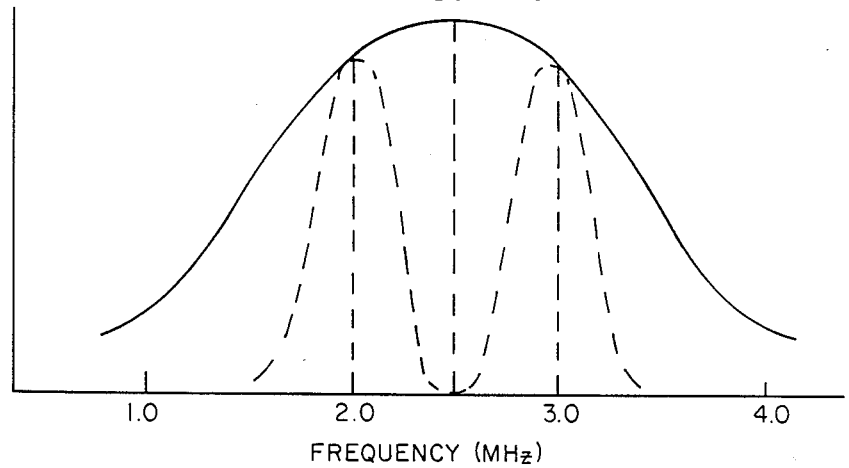
FIG. 2 is a curve illustrating the frequency spectrum of a received ultrasonic wave and curves for two narrow band filters within the frequency spectrum.

FIG. 2 is a graph illustrating the frequency spectrum of an ultrasound wave received by transducer 10 and of the backscattered wave, and both having a center frequency at 2.4 megahertz. To illustrate the invention, narrow band pass filters with a 6 dB bandwidth of 200 KHz are positioned within the spectrum at, for example, a center frequency of 2.0 megahertz and a center frequency of 3.0 megahertz. The bandpass filtering of the backscattered ultrasound signals causes a shift in amplitude distributions of the filtered signals depending on whether the reflections are from normal tissue or from diseased tissue.

Figure 3:
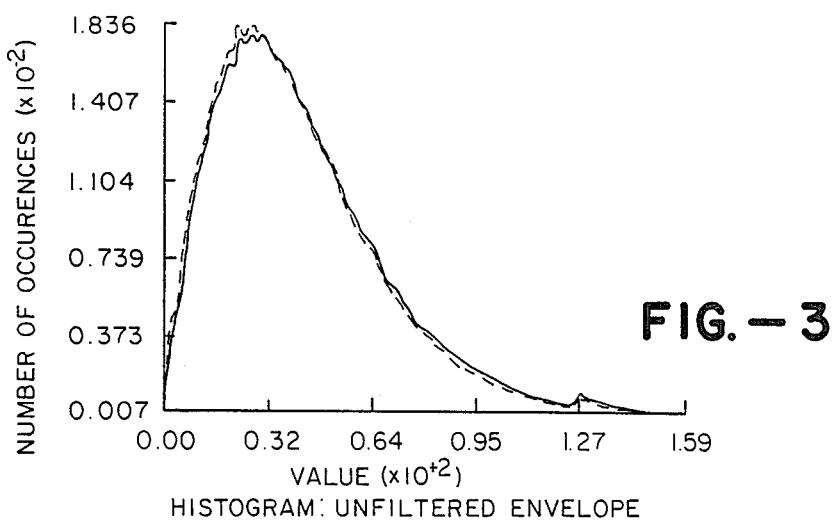
FIG. 3 is an averaged amplitude histogram of unfiltered electrical signals based on backscattered ultrasound from normal tissue and diseased tissue.

Consider now FIG. 3 which is an amplitude histogram of unfiltered electrical signals based on ultrasound reflections from normal tissue (solid line) and diseased tissue (broken line). In this case the diseased tissue is a cirrhotic liver. It will be noted that the number of occurrences for given amplitude values are essentially the same for the backscattered waves from normal and diseased tissue.

Consider now the amplitude histograms of FIGS. 4A–4F that are filtered signals lying in passbands within the spectrum of FIG. 2. FIG. 4A is a histogram for a bandpass filter with a center frequency 2.0 MHz and it is noted that the number of occurrences at higher values increases for the diseased tissue (broken line) as compared to the normal tissue (solid line). In FIG. 4B a band-pass filter at the spectrum center frequency of 2.4 MHz demonstrates that the amplitude distributions are approximately the same for both diseased and normal tissue. When the passband is placed above the center frequency of the spectrum, as in FIGS. 4C–4F, the normal tissue has a greater number of occurrences at higher amplitude values than does the diseased tissue. Apparently, the small scatterers of normal tissue backscatter ultrasound with a high dependence on frequency, whereas large scatterers present in diseased tissue are essentially frequency independent. Accordingly, based upon the amplitude distribution differences after narrow band filtering, the amplitude information can be readily used to differentiate normal from diseased tissue.

In order that the amplitude distributions following narrowband filtration reflect only differences in the types of scatterers in tissue regions of interest, compensation for alteration in the shape of the first frequency spectrum caused by frequency-dependent attenuation in tissues overlying (and possibly within) the tissue region of interest may be necessary. This compensation might be accomplished in a number of ways: the variable gain amplification settings required to acquire standardized unfiltered waveforms might be employed to estimate the effects of frequency-dependent attenuation in overlying tissues, and allow appropriate compensation of amplitude distributions following narrow band filtration.

Data recorded from tissues overlying (and possibly within) a tissue region of interest might be employed in a direct calculation of frequency-dependent attenuation in these tissues. Again, the known effects of frequency-dependent attenuation would be compensated for by appropriate alterations in amplitude distributions following narrow-band filtration. A final possibility would be the calculation of a reference power spectrum from a proximal portion of the data from a tissue region of interest; this reference spectrum could be used, along with some nominal reference spectrum of desired shape, to create a filter which would be capable of compensating for the effects of frequency-dependent attenuation in overlying tissues.

Amplitude information following narrow band filtration might be used in a variety of ways to create ultrasonic images. For example, the output of a narrow band filter of center frequency below the transducer center frequency can be weighted appropriately, as indicated in FIG. 1. With the use of such a single filter, the high amplitude occurrences can be represented by large or "bright" image points. Employing such a technique of image processing, normal tissue would be relatively dark, whereas diseased tissue would be relatively bright. Alternatively, the filtered response from tissue undergoing examination can be compared to the known response of the same filter for normal tissue; the difference between the 2 responses could be used to weigh ultrasonic images.

The use of more than one narrow band filter for image creation is another possibility. The amplitude difference between the outputs of 2 narrow band filters, with center frequencies below and above the transducer center frequency respectively, can be encoded in image format. Higher amplitude differences would be represented by "bright" image points, lower values (extending through the negative range) would be represented by relatively dark image points. Because of the differences in output of these filters for normal and diseased tissue, this technique could lead to enhanced differentiation of normal and diseased tissue. As above, the diseased tissue would be relatively bright compared to normal tissue in the images created. As with the general technique, methods as outlined previously to compensate for the effects of frequency-dependent attenuation of tissues overlying (and possibly within) the tissue region of interest might be incorporated into the image creation process. This step would be necessary for the creation of images in which only the frequency dependence of backscattering is encoded.

By so processing backscattered ultrasound signals through use of bandpass filtering and suitable weighting of the amplitude values, as above described, the detection of diseased tissue is readily obtained. While the invention has been described with reference to a specific embodiment using normal and cirrhotic liver tissue, the description is illustrative of the invention and is not to be construed as limiting the invention. Various modifications and applications may occur to those skilled in the art without departing from the true spirit and scope of the invention as defined by the appended claims.

What is claimed is:

1. A method for diagnosing disease in a region of tissue in a body using tissue backscattering characteristics, said body having tissue layers overlying said region, comprising the steps of:

applying ultrasound waves through said tissue layers to said region of tissue, said ultrasound waves having a first frequency spectrum and a center frequency, receiving backscattered ultrasound waves from said region of tissue and generating electrical signals therefrom, amplifying said electrical signals to a standardized dynamic amplitude range to compensate for attenuation of said tissue layers, bandpass filtering said electrical signals using at least one bandpass filter having a narrow pass band relative to said first frequency spectrum, said bandpass filtering step including the step of selecting a filtering band providing enhancement of backscattering characteristics of said tissue region when diseased, providing amplitude distributions of the filtered electrical signals after bandpass filtering, determining at least one statistical parameter of said amplitude distributions, said at least one parameter being indicative of said tissue backscattering characteristics, and analyzing said at least one parameter to diagnose the presence of disease in said tissue region.

2. The method as defined by claim 1 and further including the steps of deriving an image weighting function based upon said at least one statistical parameter, applying said function to said electrical signals to provide a weighted image, and displaying said weighted image as representative of the backscattering characteristics of said tissue.

3. The method as defined by claim 1 wherein said step of amplifying said electrical signals includes compensating said electrical signals for the effects of frequency-dependent attenuation in tissues overlying and within said diseased tissue.

4. The method as defined by claim 1 wherein said standardized dynamic amplitude range is based on unfiltered electrical signals generated from backscattered ultrasound waves.

5. The method as defined by claim 1 wherein said standardized dynamic amplitude range is based on narrow-band filtered electrical signals generated from backscattered ultrasound waves.

6. Apparatus for use in diagnosing disease in a region of tissue in a body using tissue backscattering characteristics, said body having tissue layers overlying said region comprising means for applying an ultrasound waves to tissue, said ultrasound waves having a first frequency spectrum and a center frequency, means for receiving ultrasound waves backscattered from said tissue and generating electrical signals therefrom, means for amplifying said electrical signals to a standardized dynamic amplitude range to compensate for attenuation of said tissue layers, at least one bandpass filter means for receiving and filtering said amplified electrical signals to provide enhancement of backscattering characteristics of said tissue region when diseased, said bandpass filter means having a narrow pass band relative to said first frequency spectrum, said bandpass filter means having a center frequency within the bounds of said first frequency spectrum, means for determining amplitude distributions of the filtered electrical signals from said bandpass filter means, means for determining at least one statistical parameter of said amplitude distributions, said at least one parameter being indicative of said tissue backscattering characteristics, and means for analyzing said at least one parameter to diagnose the presence of disease in said tissue region.

7. Apparatus as defined by claim 6 and further including means for deriving an image weighting function based upon said at least one statistical parameter, means for applying said function to said electrical signals to provide a weighted image, and means for displaying said weighted image as representative of the backscattering characteristics of said tissue.

8. Apparatus as defined by claim 6 wherein said means for amplifying said electrical signals compensates said electrical signals for the effects of frequency-dependent attenuation in tissues overlying and within said diseased tissue.

9. Apparatus as defined by claim 6 wherein said means for applying ultrasound waves and said means for receiving ultrasound waves comprise a single transducer.

* * * * *